United States Patent [19]

Klintmalm

[11] Patent Number: 5,019,092
[45] Date of Patent: May 28, 1991

[54] LIVER TRANSPLANT CLAMP

[75] Inventor: Goran B. Klintmalm, Dallas, Tex.

[73] Assignee: Pilling Company, Fort Washington, Pa.

[21] Appl. No.: 416,841

[22] Filed: Oct. 4, 1989

[51] Int. Cl.⁵ .............................................. A61B 17/28
[52] U.S. Cl. ...................................... 606/207; 81/418
[58] Field of Search ............... 606/205, 207, 158, 208; 81/420, 418, 419

[56] References Cited

U.S. PATENT DOCUMENTS

| | | | |
|---|---|---|---|
| 1,472,380 | 10/1923 | Atwood | 606/207 |
| 1,664,112 | 3/1928 | Jünemann | 606/205 |
| 2,109,147 | 2/1938 | Grosso | 606/205 |
| 3,083,711 | 8/1963 | Ramsay | 606/207 |
| 3,101,715 | 8/1963 | Glassman | 606/207 |
| 3,911,766 | 10/1975 | Fridolph et al. | 606/208 |
| 4,605,002 | 8/1986 | Rebuffat | 606/207 |
| 4,803,983 | 2/1989 | Siegel | 606/208 |
| 4,827,920 | 5/1989 | Hodge | 606/158 |

FOREIGN PATENT DOCUMENTS 0932366 7/1963 United Kingdom ................ 128/321

Primary Examiner—C. Fred Rosenbaum
Assistant Examiner—William W. Lewis
Attorney, Agent, or Firm—Howson & Howson

[57] ABSTRACT

A vascular clamp particularly suitable for use in liver transplant surgery. The free ends of pivoted handles arch toward each other and connect to the middle of elongate curved jaws which lie in substantially parallel planes when the handles are in the normal clamping position. The curvature of the jaws, projected into the parallel planes, decreases toward the ends farthest from the handles, and coincides at the other end with an arc, the extension of which smoothly merges near the pivoted connection with the handles. A bridge member joining the jaws to the handles prevent sutures from entangling on the clamp and reduces bending of the jaws at the juncture with free ends of the handles.

11 Claims, 2 Drawing Sheets

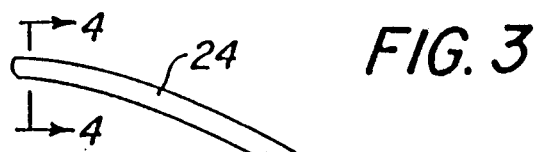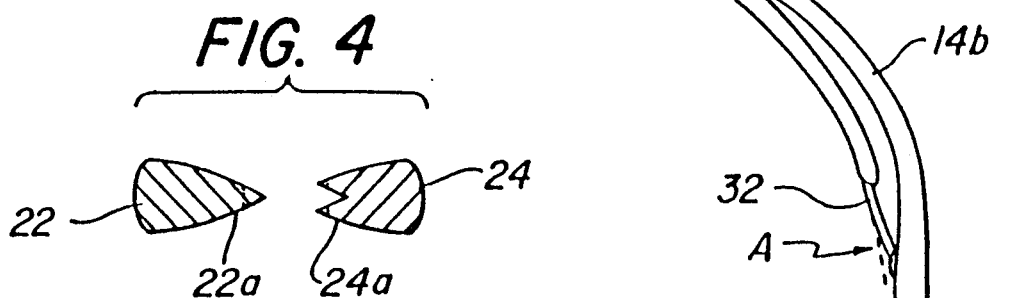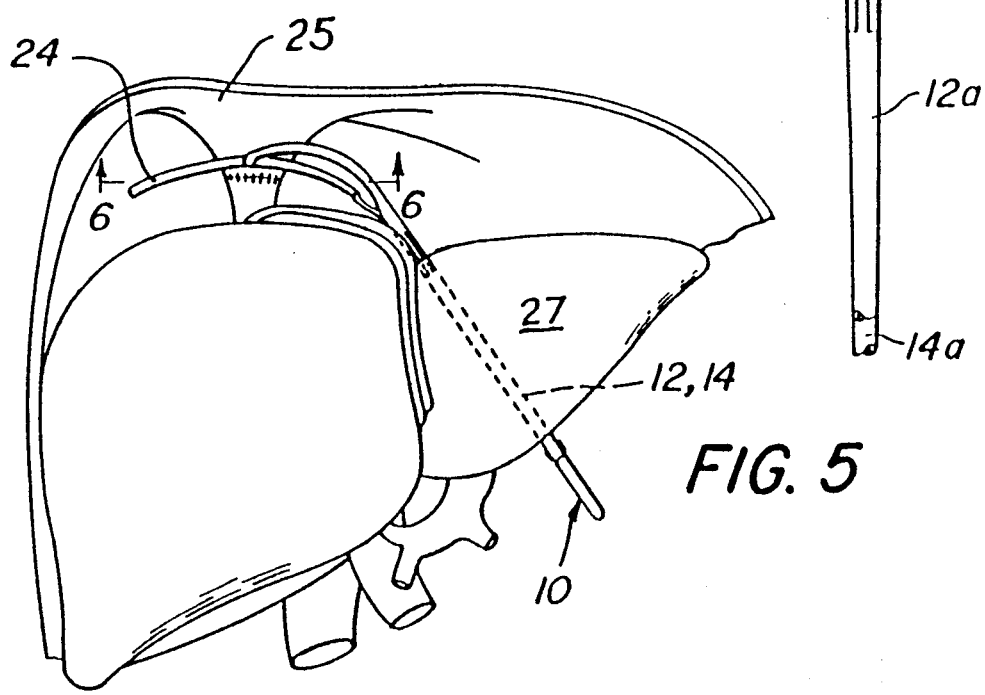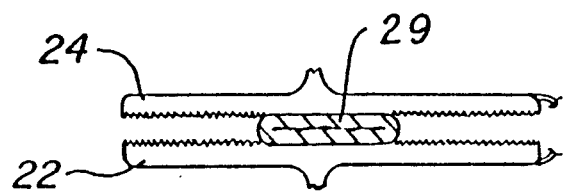

LIVER TRANSPLANT CLAMP

BACKGROUND OF THE INVENTION

The present invention relates generally to surgical instruments for occluding blood vessels during a surgical procedure, and more particularly to a vascular clamp suitable for closing the suprahepatic portion of the inferior vena cava when transplanting a liver.

Surgical instruments such as forceps, hemostats and clamps, for temporary occlusion of blood vessels, come in various sizes and configurations to meet the specific requirements. For example, the Satinsky clamp, manufactured by Pilling Company, Fort Washington, Pa., is among the more popular and versatile of cardiac clamps and is designed to provide a non-crushing grip on the vena cava. However, the configuration of this clamp and others of the prior art do not meet the special needs in transplanting livers. The problem normally encountered is that these clamps, when used to occlude the suprahepatic inferior vena cava during surgery, do not fully close near the tips due to the amount of tissue between the jaws. This can also cause the jaws to slip off the upper vena cava cuff and produce a potentially life-threatening situation. If by mischance the jaws should slip, their tips might dig into the superior border of the right hepatic lobe of the liver causing lacerations and sometimes difficult bleeding. A more serious consequence might be that the tips penetrate the right hepatic vein.

SUMMARY OF THE INVENTION

Accordingly, it is an object of the present invention to provide a vascular clamp with jaws suitable for uniformly and securely closing a blood vessel across its entire compressed width.

Another object is to provide a vascular clamp for occluding the suprahepatic inferior vena cava during liver transplant surgery, which does not interfere with tissue medial to liver parenchyma, which minimizes the risk of the vena cava slipping out of the clamp, and which prevents sutures from entangling on the clamp when anastomosis of the upper vena cava is performed.

A further object of the invention is to provide a vascular clamp which is particularly suitable for clamping a thin wall vena cava prone to rupture.

Still another object is to provide a vascular clamp in which the jaws delicately but completely occlude a blood vessel without danger of crushing or causing undue damage to the intima, and which minimizes trauma at the occluded vessel and adjacent structures.

Briefly, these and other objects and aspects of the invention are accomplished with a liver transplant clamp in which the free ends of pivoted handles connect to the approximate middle of curved jaws characterized by a double row of serrated teeth opposing a single row. In the clamping position, the rows lie in substantially parallel planes normal to the plane in which the handles move. Within the parallel planes, the curvature of the jaws decreases toward the ends farthest from the handles, and coincides at the other ends with an arc which smoothly merges with the plane of the handles, whereby maximum separation is obtained between the jaws and the dome of the right hepatic lobe when the clamp is firmly secured on the suprahepatic portion of the inferior vena cava. Braces connected between the jaws and the handles prevent sutures from catching on the clamp when vena cava anastomosis is performed, and provide rigidity to the jaws.

Other objects and novel features of the invention will become more apparent from the following detailed description when considered in conjunction with the accompanying drawings.

BRIEF DESCRIPTION OF THE DRAWINGS

FIG. 3 is a side elevation view of the distal end of the clamp of FIG. 1;

FIG. 4 is a cross sectional view of the jaws of the clamp taken along the line 4—4 of FIG. 3;

FIG. 5 is an anterior view of a liver with the clamp of FIG. 1 secured to the suprahepatic inferior vena cava; and FIG. 6 is a cross sectional view of the vena cava taken along the line 6—6 of FIG. 5.

DESCRIPTION OF THE PREFERRED EMBODIMENT

Figure 1:
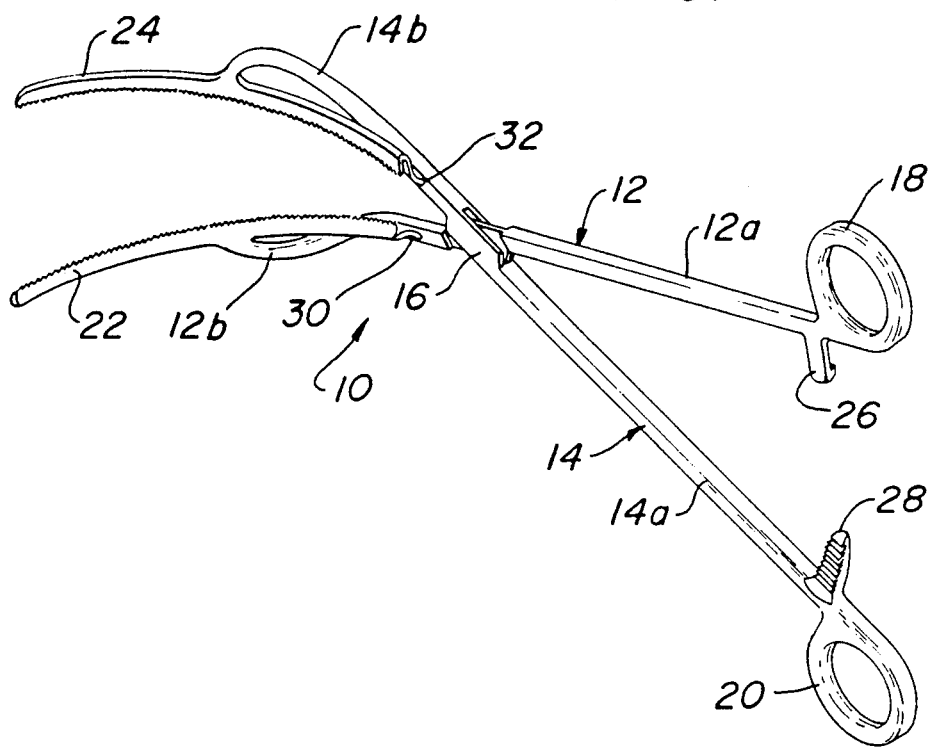
FIG. 1 is an isometric view of a vascular clamp constructed according to the invention suitable for use in liver transplant surgery.
Figure 2:
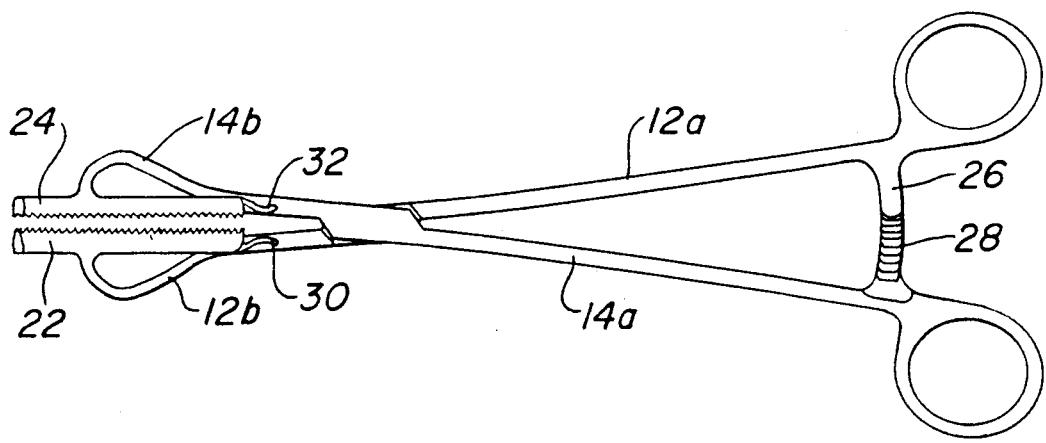
FIG. 2 is a plan view of the clamp of FIG. 1.

Referring now to the drawings wherein like characters designate like or corresponding parts throughout the several views, there is shown in FIG. 1 a vascular clamp 10 suitable for use in liver transplant surgery comprising a pair of elongate handles 12 and 14 of steel, such as Type 410X martinsitic stainless steel, pivoted together in the middle by a substantially stress-free hinge integrally formed in a box lock joint 16 such as disclosed in U.S. Pat. No. 3,952,749 to John Fridolph et al. Handles 12 and 14 include substantially straight arms 12a and 14a extending from joint 16 which may be manipulated in scissors-like motion by finger grips 18 and 20. The handles further include compound curved arms 12b and 14b extending oppositely of arms 12a and 14a from joint 16. As shown in FIG. 2, a projection of arms 12b and 14b into the plane of arms 12a and 14a forms opposed arches; and, as shown in FIG. 3, projections of arms 12b and 14b into respective planes along the length of arms 12a and 14a and normal to the plane of arms 12a and 14a form coaligned arches.

Opposed elongate jaws 22 and 24 are integrally joined, as by welding, midway along their lengths to the distal ends of arms 12b and 14b. As best illustrated in FIG. 2, jaws 22 and 24 lie in planes normal to the plane in which arms 12a and 14a articulate; and, when in a normal clamping position as shown, they are substantially parallel to each other. In such a configuration, a clamping force imparted to handles 12 and 14 is diffused more evenly across the compressed width of a blood vessel centered between the jaws. Locking lugs 26 and 28 extending from arms 12a and 14a adjacent grips 18 and 20 define a ratchet-and-tooth arrangement for interengaging the handles when jaws 22 and 24 are squeezed toward closing. The resilience of the handles in bending determines the clamping force at the jaws.

Referring now to FIG. 3, it will be noted that the curvature of jaws 22 and 24 within the parallel planes thereof decreases from the ends nearest to the handles toward the ends farthest from handles 12 and 14, and coincides at the nearest ends with an arc A, the extension of which tangentially and smoothly merges near hinge 16 with the plane of arms 12a and 14a. A typical clamp (large size) suitable for liver transplant surgery, as above-described, is constructed with an overall length of 25 cm, (measured in the plane of handles 12 and 14) and includes jaws with a chord length of 9.5 cm and radii of curvature of approximately 9.5 cm and 14 cm at the nearest and farthest ends, respectively. This composite curvature relative to the handles provides a non-interfering and relatively safe separation of the tips of jaws 22 and 24 from the dome of the right hepatic lobe of the liver while maintaining a firm grip across the width of the compressed suprahepatic inferior vena cava.

As shown in FIG. 4, jaws 22 and 24 comprise, respectively, a single row of serrated teeth 22a opposed by a double row of serrated teeth 24a, the courseness being selected to prevent slippage of the tissue and minimize trauma at the clamp site.

To prevent sutures from catching on the jaws while anastomising the clamped blood vessel, braces 30 and 32 bridge the opening between the proximal ends of jaws 22 and 24 and handles 12 and 14. Braces 30 and 32 also provide a secondary clamping force to resist any deflection due to unequal moments of force about the junction of jaws 22 and 24 and arms 12b and 14b.

The manner in which clamp 10 may be utilized in a liver transplant surgical procedure is illustrated in FIGS. 5 and 6 in which the jaws are shown clamped immediately above the sutured suprahepatic inferior vena cava 25. Jaws 22 and 24 preferably reach the upper vena cava by extending handles 12 and 14 beneath the left lobe 27 of the liver and clamp the cuff 29 between the jaws in the manner illustrated in FIG. 6. It is important to place jaws 22, 24 horizontally across the vena cava with the cuff 29 placed approximately in the middle third of the jaws making sure there is enough tissue in the bite to prevent rupture of the cava due to pulling on the clamp if the vena cava wall is thin.

Some of the many advantages and novel features of the invention should now be readily apparent. For example, a vascular clamp is provided which is particularly suitable for occluding the superhepatic inferior vena cava during liver transplant surgery. In the event the jaws should slip off the cuff, the curvature of the clamp provides a non-interfering and relative safe separation of the tips of the jaws for minimizing the risk of lacerating the right hepatic lobe or of penetrating the right hepatic vein. The jaws of the clamp are so positioned to insure uniform and secure closing of the blood vessel across its entire compressed width without crushing or causing undue damage to the intima as well as minimal trauma to the clamping site and adjacent structures. The clamp is particularly suitable for clamping a thin wall vena cava which is prone to rupture, and includes provisions for preventing sutures from entangling in the jaws during anastomosis.

It will be understood, of course, that various changes in the details, steps, and arrangement of parts, which have been herein described and illustrated in order to explain the nature of the invention, may be made by those skilled in the art within the principle and scope of the invention as expressed in the appended claims.

I claim:

1. A clamp comprising:
a pair of elongate handles each having opposed ends, said handles being pivotally connected on an axis intermediate opposed ends thereof and movable between open and closed positions in a generally longitudinal plane; and
a pair of elongate curved jaws each having opposed ends, said jaws being fixed to adjacent ones of said handle ends, said jaws having curved faces lying in lateral planes generally aligned with respective ones of said handles and normal to the longitudinal plane, the jaw ends being proximal to the pivot axis smoothly merging with said handles near the pivot axis on arcs in the lateral planes.

2. A clamp according to claim 1 wherein:
the faces of said jaws are substantially parallel to each other in the closed position with tissue or the like between said jaws.

3. A clamp according to claim 1 wherein:
the curvature of said jaws decreases from said proximal ends to distal ends.

4. A clamp according to claim 3 further comprising:
a pair of bridge members connected between respective ones of the handles and the ends of said jaws proximal thereto.

5. A clamp according to claim 4 further comprising:
locking means extending from said handles for maintaining the closed position thereof.

6. A clamp adapted for securely occluding the suprahepatic inferior vena cava during liver transplant surgery, comprising:
a pair of shafts each having opposed ends, said shafts being pivotally connected to each other with a handle at one end of each of said shafts, said shafts being pivotable in a generally longitudinal plane;
a pair of jaws each having opposed ends, said jaws being fixed to the other end of each of said shafts for manipulating said handles, the faces of said jaws formed to grip the upper vena cava securely with the shafts disposed out of the surgical site, said jaws disposed on one side of said longitudinal plane and lying in lateral planes generally aligned with respective ones of said shafts and normal to the longitudinal plane, the ends of said jaws proximal to said handles smoothly merging into the longitudinal plane near the pivotal axis.

7. A clamp according to claim 6 wherein:
said gripping faces are substantially parallel in the closed position with tissue between said gripping faces.

8. A clamp according to claim 7 wherein:
the radius of curvature of said jaws in the lateral planes increases from the ends nearest to said shafts to the ends farthest from said shafts.

9. A clamp according to claim 6 further comprising:
braces connected between said jaws and said shafts for preventing sutures from entangling on the clamp during anastomosis of the vena cava.

10. A vascular clamp suitable for liver transplant surgery and similar procedures comprising, in combination:
a pair of elongate members pivotally connected together on an axis intermediate opposite ends thereof forming first and second pairs of arms, the arms of said first pair movable in a generally longitudinal plane for manipulating said second pair relative to each other between a closed position and an open position, each arm of said second pair terminating in an end laterally disposed to one side of said longitudinal plane; and
a pair of elongate jaws joined intermediate opposite ends thereof respectively to the ends of said second pair of arms, said jaws having opposed arcuate clamping faces lying in lateral planes generally aligned with respective arms of said first pair and normal to the longitudinal plane and smoothly merging near the pivot axis with the longitudinal plane, the curvature of said jaws decreasing from the ends nearest to said members to the ends farthest from said member.

11. A vascular clamp suitable for liver transplant surgery and similar procedures comprising, in combination:
- a pair of elongate members pivotally connected together on an axis intermediate opposite ends of said members and forming first and second pairs of arms, the arms of said first pair movable in a generally longitudinal plane for manipulating said second pair relative to each other between a closed position and an open position, each arm of said second pair terminating in an end laterally disposed to one side of said longitudinal plane;
- a pair of elongate jaws joined intermediate opposite ends of said jaws respectively of the ends of said second pair of arms, said jaws having opposed arcuate clamping faces lying in lateral planes generally aligned with respective arms of said first pair and normal to the longitudinal plane and merging toward the pivot axis; and
- a pair of braces connected between respective ones of said second pair of arms and the ends of said jaws proximal thereto.

* * * * *